United States Patent [19]

Cobb

[11] 3,998,853
[45] Dec. 21, 1976

[54] 13-OXATETRACYCLO[8.2.1$^{2,9}$.0.0$^{3,8}$]TRI-DEC-5-ENE-1,5,6,10-TETRACARBONITRILE

[75] Inventor: Raymond L. Cobb, Bartlesville, Okla.

[73] Assignee: Phillips Petroleum Company, Bartlesville, Okla.

[22] Filed: Dec. 4, 1975

[21] Appl. No.: 637,500

[52] U.S. Cl. .................. 260/346.2 M; 260/251 R; 260/239.75; 260/239.9; 260/307 R; 260/290 R; 260/307 H; 260/302 R; 260/326.33; 260/329 F; 260/346.1 R

[51] Int. Cl.$^2$ ..................................... C07D 307/77

[58] Field of Search ............ 260/346.2 R, 346.2 M

[56] References Cited

UNITED STATES PATENTS

| | | | |
|---|---|---|---|
| 2,905,730 | 9/1959 | Ray et al. | 260/251 R |
| 3,175,013 | 3/1965 | Smith | 260/251 R |
| 3,197,525 | 7/1965 | Schaeffer | 260/251 R |
| 3,247,177 | 4/1966 | Hepp | 260/251 R |
| 3,441,505 | 4/1969 | Schmiedel | 260/251 R |
| 3,470,248 | 9/1969 | Brotherton et al. | 260/251 R |
| 3,494,953 | 2/1970 | Wagner | 260/251 R |
| 3,717,623 | 2/1973 | Ruyle | 260/251 R |
| 3,855,195 | 12/1974 | Suda et al. | 260/251 R |

OTHER PUBLICATIONS

Kobe; Adv. Petro. Chemistry and Refining, vol. 6, (1962), pp. 119–167.
J. Am. Chem. Soc. 86, 1964, No. 23, pp. 5140–5144.

*Primary Examiner*—Lewis Gotts
*Assistant Examiner*—D. R. Phillips

[57] ABSTRACT

13-Oxatetracyclo[8.2.1$^{2,9}$.0.0$^{3,8}$]tridec-5-ene-1,5,6,10-tetracarbonitrile; clathrates thereof with monocyclic unsubstituted aromatic compounds; and methods of separating organic admixtures.

1 Claim, No Drawings

13-OXATETRACYCLO[8.2.1$^{2,9}$.0.0$^{3,8}$]TRIDEC-5-ENE-1,5,6,10-TETRACARBONITRILE

FIELD OF THE INVENTION

The invention relates to novel compositions of matter. In a further aspect, the invention relates to methods of preparation of novel compositions of matter. In a further aspect, the invention relates to novel methods of separation.

BACKGROUND OF THE INVENTION

The removal of traces of monocyclic unsubstituted aromatic compounds from related compounds often is difficult. For example, scavenging of small amounts of benzene from cyclohexene or cyclohexadiene is difficult by normal procedures. It would be very helpful to be able to provide some method of "picking up" traces of such aromatics and providing easier separations.

BRIEF DESCRIPTION OF THE INVENTION

I have discovered the novel compound 13-oxatetracyclo[8.2.1$^{2,9}$.0.0$^{3,8}$]tridec-5-ene-1,5,6,10-tetracarbonitrile. I have further discovered that this compound forms clathrates (inclusion complexes) with monocyclic unsubstituted aromatic compounds. The novel compound exhibits unusual selective behavior in forming stable clathrates (inclusion complexes) with monocyclic unsubstituted aromatic compounds, such as benzene, pyridine, furan, pyrrole, thiophene, and the like. These clathrates are stable up to modest temperatures, of about 140° C., above which the included aromatic compound readily separates. The recovered host compound of my discovery can then be used again to effect further separations.

Inclusion complexes (clathrates) are considered mixtures, not true compounds, in the sense that the molecules of one of the components are contained within the framework of the other component, though the two components are present in constant proportions. Clathrate compounds are inclusion complexes in which molecules of one substance are completely caged, so to speak, within the other. The formation of these inclusion complexes offers a means of separating molecules which are chemically similar but physically different. The 13-oxatetracyclo[8.2.1$^{2,9}$.0.0$^{3,8}$]tridec-5-ene-1,5,6,10-tetracarbonitrile is a new and very useful compound which readily forms novel clathrates with monocyclic unsubstituted aromatic compounds.

DETAILED DESCRIPTION OF THE INVENTION

The novel compound which is basic to the new compositions of matter and processes of my invention is 13-oxatetracyclo[8.2.1$^{2,9}$.0.0$^{3,8}$]tridec-5-ene-1,5,6,10-tetracarbonitrile.

The novel composition of matter 13-oxatetracyclo[8.2.1$^{2,9}$.0.0$^{3,8}$]tridec-5-ene-1,5,6,10-tetracarbonitrile, represented by the formula (A) below, can be prepared by the reaction of the furan adduct of cyclobutene-1,2-dicarbonitrile with 1,3-butadiene-2,3-dicarbonitrile.

The preparatory sequence can be illustrated by:

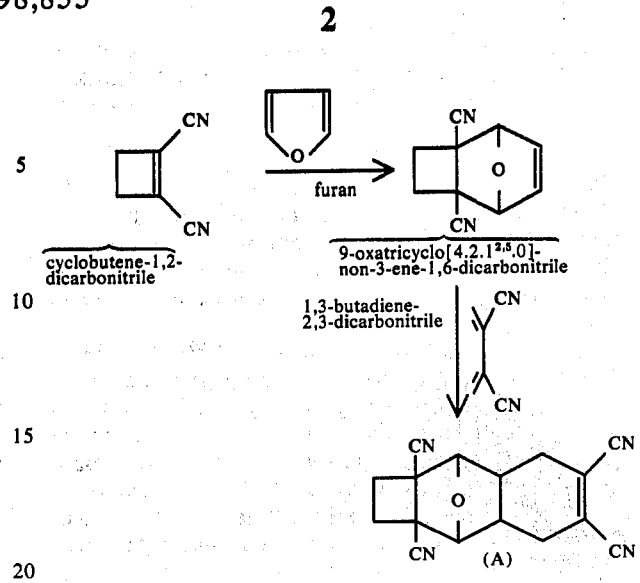

In the preparation of the 13-oxatetracyclo[8.2.1$^{2,9}$.0.0$^{3,8}$]tridec-5-ene-1,5,6,10-tetracarbonitrile compound of my discovery, a furan adduct of cyclobutene-1,2-dicarbonitrile is prepared by contacting cyclobutene-1,2-dicarbonitrile with furan employing any suitable reaction conditions, for example, a mole ratio of cyclobutene-1,2-dicarbonitrile:furan of about 1:10 to 10:1, at a temperature of about 0° to 100 C., employing autogenous pressures or higher, for a time of such as less than 1 hour up to several days, such as 5 days or even longer, employing conventional equipment such as glass-lined vessels, metal autoclaves, and the like.

After the reaction period, the furan adduct of cyclobutene-1,2-dicarbonitrile can be separated and isolated from the crude reaction mixture by any suitable separation means, such as by extraction with a volatile solvent followed by evaporation of the volatile solvent.

The furan adduct of cyclobutene-1,2-dicarbonitrile then is contacted with 1,3-butadiene-2,3-dicarbonitrile employing any suitable reaction conditions, for example, a molar ratio of the furan adduct of cyclobutene-1,2-dicarbonitrile:1,3-butadiene-2,3-dicarbonitrile in the range of about 1:10 to 10:1, at any convenient temperature, such as a temperature in the range of about 10° to 200° C., at autogenous pressures or higher, employing a chemically inert clathratable or nonclathratable diluent.

Such diluent conveniently is a clathratable compound, a monocyclic nonsubstituted aromatic compound such as benzene, furan, pyridine, pyrrole, pyrimidine, pyrazine, pyridazine, thiazole, isothiazole, oxazole, isooxazole, imidazole, and the like, preferably and conveniently benzene. Conducting this step of the preparation reaction scheme in a clathratable diluent results in a clathrate which appears as a substantially insoluble precipitate in the diluent. The clathrate can be readily separated by convenient means, such as filtering, centrifuging, or the like. The separated clathrate then can be treated so as to remove the included nonsubstituted aromatic diluent so as to recover the 13-oxatetracyclo[8.2.1$^{2,9}$.0.0$^{3,8}$]tridec-5-ene-1,5,6,10-tetracarbonitrile. The monocyclic aromatic diluent can be volatized off at about 140° C. or higher, depending on the nature of the included component, or can be removed by recrystallizing the clathrate from a nonclathratable diluent, such as acetone or the like in which the 13-oxatetracyclo[8.2.1$^{2,1}$.0.0$^{3,8}$]tridec-5-ene-1,5,6,10-tetracarbonitrile has limited solubility dependent on temperature.

Alternatively, 13-oxatetracyclo[8.2.1$^{2,9}$.0.0$^{3,8}$]tridec-5-ene-1,5,6,10-tetracarbonitrile can be isolated directly by filtration if a nonclathratable diluent such as a substituted aromatic hydrocarbon such as toluene, or halogenated aliphatic such as carbon tetrachloride or methylene chloride, or a lower ketone such as acetone, is used.

The novel 13-oxatetracyclo[8.2.1$^{2,9}$.0.0$^{3,8}$]tridec-5-ene-1,5,6,10-tetracarbonitrile compound that I have discovered is utilizable in preparing a variety of novel inclusion complexes. The inclusion complexes can be prepared by stirring a portion of the 13-oxatetracyclo[8.2.1$^{2,9}$.0.0$^{3,8}$]-tridec-5-ene-1,5,6,10-tetracarbonitrile in the monocyclic unsubstituted aromatic compound for a sufficient time, at any convenient temperature below the decomposition point of the clathrate, such as in the range of about 10° to 120° C., at any convenient pressure, autogenous pressures or higher. The resulting clathrate is insoluble in the monocyclic unsubstituted aromatic compound, and can be recovered by any convenient means, such as filtration, centrifuging, or the like.

An alternative method of preparing the novel clathrates comprises dissolving a suitable amount of 13-oxatetracyclo[8.2.1$^{2,9}$.0.0$^{3,8}$]tridec-5-ene-1,5,6,10-tetracarbonitrile in a suitable nonclathratable diluent-solvent, such as acetone, carbon tetrachloride, methylene chloride, or the like, at temperatures below about 140° C., preferably and conveniently at room temperature, and thereafter to add to the solution any suitable amount of the aromatic compound to be clathrated, such as a molar ratio of the monocyclic nonsubstituted aromatic compound to the 13-oxatetracyclo[8.2.1$^{2,9}$.0.0$^{3,8}$]tridec-5-ene-1,5,6,10-tetracarbonitrile of about 0.5 to 1000. The resulting clathrate may be recovered by removing the volatile solvents to cause separation of the insoluble clathrate. The recovered clathrate can be washed with a nonclathratable diluent, such as diethyl ether, and dried up to such as about 120° C. to remove traces of solvent, unbound aromatic component, and washing solvent.

Novel clathrates can be obtained with my novel 13-oxatetracyclo[8.2.1$^{2,9}$.0.0$^{3,8}$]tridec-5-ene-1,5,6,10-tetracarbonitrile and monocyclic unsubstituted aromatic compounds selected from benzene, pyridine, furan, thiophene, pyrrole, pyrazine, pyrimidine, pyridazine, thiazole, isothiazole, oxazole, isooxazole, pyrazole, imidazole, and the like. It is also contemplated that the partially deuterated and perdeuterated derivatives of the foregoing compounds can also be used in an aspect of my invention to form novel clathrates, such as perdeuterobenzene.

The novel inclusion complexes of my discovery on the average consist of about two molecules of 13-oxatetracyclo[8.2.1$^{2,9}$.0.0$^{3,8}$]tridec-5-ene-1,5,6,10-tetracarbonitrile in association with each aromatic molecule. Utilizing the symbol A to represent the host molecule 13-oxatetracyclo[8.2.1$^{2,9}$.0.0$^{3,8}$]tridec-5-ene-1,5,6,10-tetracarbonitrile, then the clathrates also can be represented by the approximate formula (A)$_2$ArH wherein ArH represents the guest molecule of the unsubstituted monocyclic aromatic compound and their partially deuterated and per deuterated derivatives.

My clathrates find utility in extracting traces of monocyclic unsubstituted aromatic compounds from other nonclathratable solvents, such as benzene from cyclohexane or cyclohexadiene; perdeuterobenzene from other NMR solvents; pyrrole from N-methylpyrrole; pyridine from picolines; and the like. In general, the purification method simply involves contacting the impure nonclathratable solvent containing small amounts of clathratable contaminants with a suitable amount of my novel 13-oxatetracyclo[8.2.1$^{2,9}$.0.0$^{3,8}$]-tridec-5-ene-1,5,6,10-tetracarbonitrile in accordance with the amount of the impurity contained in the solvent, permitting the clathrate to form at a moderate to low temperature wherein it is substantially insoluble, and filtering off or otherwise removing insoluble matter from the now-purified solvent. The insoluble clathrate then can be regenerated simply by heating to at least the composition temperature, such as about 140° to 200° C., and recovering the novel 13-oxatetracyclo[8.2.1$^{2,9}$.0.0$^{3,8}$]tridec-5-ene-1,5,6,10-tetracarbonitrile for repeated use.

EXAMPLES

The examples provided are designed to assist those skilled in the art to which my invention most nearly appertains to an understanding of my invention. The examples are designed to be a part of my disclosure including claims, and hence the particular materials employed, operating conditions, ratios, and the like, should be considered as exemplary and not as limitative.

EXAMPLE I

Preparation of 13-oxatetracyclo[8.2.1$^{2,9}$.0.0$^{3,8}$]tridec-5-ene-1,5,6,10-tetracarbonitrile A mixture of 50 g (0.48 mole) cyclobutene-1,2-dicarbonitrile and 6.8 g (0.1 mole) furan was heated in a rocking autoclave at 80° C. for 5 days. The reaction mixture was contacted with a mixture of tetrahydrofuran (THF) and diethyl ether to give a THF-ether solution and 10.75 g of insoluble residue. The insoluble matter was separated out. The THF-ether solution was concentrated to give 46 g of an oil. Admixture of this oil with about 200 ml diethyl ether gave 7.91 g (0.0465 mole) 9-oxatricyclo[4.2.1$^{2,5}$.0]non-3-ene-1,6-dicarbonitrile with a melting point of 150° to 153° C.

A mixture of 1.72 g (0.01 mole) of 9-oxatricyclo[4.2.1$^{2,5}$.0]non-3-ene-1,6-dicarbonitrile, 1.05 g (0.01 mole) 1,3-butadiene-2,3-dicarbonitrile, and 0.1 g hydroquinone was stirred under reflux in 50 ml of benzene for about 24 hours. The small amount of hydroquinone was included as a polymerization inhibitor for the 1,3-butadiene-2,3-dicarbonitrile. A white precipitate gradually appeared. The admixture was filtered hot to give 1.90 g of the benzene clathrate of 13-oxatetracyclo[8.2.1$^{2,9}$.0.0$^{3,8}$]tridec-5-ene-1,5,6,10-tetracarbonitrile. The benzene was separated by volatizing off at about 140° C., and the novel compound of my invention was examined. The compound exhibited a melting point of about 338° to 340° C. Using (A) to represent my novel host compound, the benzene clathrate can be represented by (A)$_2$·C$_6$H$_6$.

The above steps were repeated, except employing hot toluene for a contacting time of about 20 hours, to result in about 2.2 grams of 13-oxatetracyclo[8.2.1$^{2,9}$.0.0$^{3,8}$]tridec-5-ene-1,5,6,10-tetracarbonitrile. No clathrate was detectable.

A further preparation employed 1,3-butadiene-2,3-dicarbonitrile in a condensation reaction with 9-oxatricyclo[4.2.1$^{2,5}$.0]non-3-ene-1,6-dicarbonitrile utilizing methylene chloride as diluent under room temperature conditions and a contacting time of about 5 days. By this method, a conversion of about 50 percent was obtained based on the 9-oxatricyclo[4.2.1$^{2,5}$.0]non-3-ene-1,6-dicarbonitrile, resulting in nearly 100 percent ultimate yields of 13-oxatetracyclo[8.2.1$^{2,9}$.0.0$^{3,8}$]tridec-5-ene-1,5,6,10-tetracarbonitrile.

EXAMPLE II

Preparation of Clathrates

Preparations of some of the novel clathrate compounds of my invention involving 13-oxatetracyclo[8.2.1$^{2,9}$.0.0$^{3,8}$]tridec-5-ene-1,5,6,10-tetracarbonitrile was carried out with a variety of unsubstituted monocyclic aromatic compounds.

In Method S, the inclusion compounds were prepared by stirring 0.25 to 0.5 g of 13-oxatetracyclo[8.2.1$^{2,9}$.0.0$^{3,8}$]tridec-5-ene-1,5,6,10-tetracarbonitrile in an excess of the monocyclic unsubstituted aromatic compound for contacting times of 2 to 3 days. Filtration of insoluble material and washing thoroughly with diethyl ether yielded the appropriate clathrate.

In a alternative Method D, 0.5 g of 13-oxatetracyclo-[8.2.1$^{2,9}$.0.0$^{3,8}$]tridec-5-ene-1,5,6,10-tetracarbonitrile was dissolved in about 200 ml acetone, and then between 2 and 25 g of the monocyclic unsubstituted aromatic compound was added to the acetone solution. The clathrate in this instance was isolated by boiling off the acetone and excess aromatic compound. The residual material, the clathrate, then was washed with dry diethyl ether and dried at a temperature of about 20° to 120° C. Each of the clathrates was studied to determine the decomposition temperature at which the guest molecule, the monocyclic unsubstituted aromatic compound, was released from my novel 13-oxatetracyclo[8.2.1$^{2,9}$.0.0$^{3,8}$]tridec-5-ene-1,5,6,10-tetracarbonitrile.

Efforts were made to prepare clathrates with a variety of substituted aromatic compounds such as toluene, and with unsubstituted polycyclic aromatics such as naphthalene, but all such attempts met with failure.

In addition to the thermal analysis data (Table I) on the aromatic inclusion compounds, elemental analyses were also determined (Table II) and these analyses were in good agreement with the proposed clathrate composition.

Table II

Elemental Analyses of Aromatic Inclusion Compounds with 13-Oxatetracyclo[8.2.1$^{2,9}$.0.0$^{3,8}$]tridec-5-ene-1,5,6,10-tetracarbonitrile

| Aromatic ArH Compound | Calculated for (C$_{16}$H$_{12}$N$_4$O)$_2$ · ArH | | | | Found | | | |
|---|---|---|---|---|---|---|---|---|
| | C | H | N | S | C | H | N | S |
| Benzene | 72.4 | 4.8 | 17.8 | | 72.3 | 4.8 | 18.1 | |
| Pyridine | 70.3 | 4.6 | 20.0 | | 69.9 | 5.0 | 20.4 | |
| Furan | 69.7 | 4.6 | 18.1 | | 69.0 | 4.5 | 17.9 | |
| Thiophene | 67.9 | 4.4 | 17.6 | 5.0 | 66.2 | 3.9 | 17.3 | 5.5 |
| Pyrrole | 69.8 | 4.7 | 20.4 | | 69.3 | 4.4 | 19.8 | |

(A)$_2$ · ArH wherein (A) represents 13-oxatetracyclo[8.2.1$^{2,9}$.0.0$^{3,8}$]tridec-5-ene-1,5,6,10-tetracarbonitrile.

The thermal stability of the benzene clathrate of 13-oxatetracyclo[8.2.1$^{2,9}$.0.0$^{3,8}$]tridec-5-ene-1,5,6,10-tetracarbonitrile was examined in a melting point capillary tube. A 0.1370 g sample of the benzene clathrate maintained for 71 minutes at 200° C. showed a weight loss of 0.0156 g, and after 150 minutes at 200° C. showed a weight loss of 0.0158 g (11.6 weight percent). This 11.6 weight percent loss is in good agreement with the result given in Table I indicating about 12 weight percent benzene in the inclusion compound. These results correspond to about 13 weight percent benzene (calculated) for the clathrate composition (A)$_2$·C$_6$H$_6$ wherein (A) represents 13-oxatetracyclo[8.2.1$^{2,9}$.0.0$^{3,8}$]tridec-5-ene-1,5,6,10-tetracarbonitrile.

The disclosure, including data, illustrates the value and effectiveness of my invention. The examples, the knowledge and background of the field of the invention and general principles of chemistry and other applicable sciences, have formed the bases from which the Table I Characterization Data on Aromatic Inclusion Compounds of 13-Oxatetracyclo[8.2.1$^{2,9}$.0.0$^{3,8}$]tridec-5-ene-1,5,6,10-tetracarbonitrile

| Guest Molecule in Inclusion Compound | Preparation Method | Temperature[a] at which the Guest Molecule is Expelled | Weight % Guest Molecule[b] in Inclusion Compound |
|---|---|---|---|
| Benzene | S | 148 | 12 |
| Pyridine | D | 140 | 12 |
| Furan | S | 143 | 10–11 |
| Thiophene | S | 145 | 11 |
| Pyrrole | S | 165 | 10 |

[a]From differential thermal analysis data.
[b]From thermal gravimetric analysis data; 10–12 weight percent range corresponds to approximately (A)$_2$ · ArH wherein (A) represents 13-oxatetracyclo-[8.2.1$^{2,9}$.0.0$^{3,8}$]tridec-5-ene-1,5,6,10-tetracarbonitrile and ArH represents the unsubstituted aromatic guest molecule.

The results in Table I show that the guest molecules in the listed clathrates (inclusion complexes) constitute about 10 to 12 weight percent of the compositions, and that the inclusion compounds are thermally stable up to the temperature range of about 140° to 165° C. with the pyrrole-containing clathrate exhibiting the greatest thermal stability.

broad descriptions of the invention including the ranges of conditions and the generic groups of operant components have been developed, which have formed the bases for my claims here appended.

I claim:
1. 13-Oxatetracyclo[8.2.1$^{2,9}$.0.0$^{3,8}$]tridec-5-ene-1,5,6,10-tetracarbonitrile.

* * * * *